United States Patent [19]

Chignac et al.

[11] 4,246,282
[45] Jan. 20, 1981

[54] ω-DIALKYLALKANOIC ACID DERIVATIVES USED TO INDUCE ANTIANOXIC ACTIVITY

[75] Inventors: Michel Chignac, Sisteron; Claude Grain, Volonne; Fernand Jammot, Sisteron; Charles Pigerol, Saint-Ouen; Pierre L. Eymard, Fontaine; Madeleine Combet (épse Broll), St. Egreve, all of France

[73] Assignee: Labaz, Paris, France

[21] Appl. No.: 46,432

[22] Filed: Jun. 7, 1979

[51] Int. Cl.³ .............................................. A61K 31/16
[52] U.S. Cl. ..................................................... 424/320
[58] Field of Search .......................................... 424/320

[56] References Cited

U.S. PATENT DOCUMENTS 3,988,472   10/1976   Pigerol et al. ...................... 424/320

FOREIGN PATENT DOCUMENTS 760114   10/1956   United Kingdom .

Primary Examiner—Stanley J. Friedman
Attorney, Agent, or Firm—Mason, Kolehmainen, Rathburn & Wyss

[57] ABSTRACT

ω-Dialkylalkanoic acid derivatives of the formula:

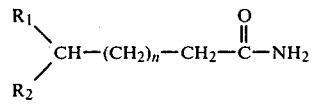

in which $R_1$ and $R_2$, which can be the same or different, each represent an alkyl radical having from 1 to 4 carbon atoms and n represents 0, 1, 2 or 3.

They possess a competitive inhibitory activity with respect to γ-aminobutyric α-ketoglutaric transaminase as well as antianoxic and anticonvulsant properties and they are useful for treating central neurological disorders, whether resulting or not from cerebral ischemia, and disorders relating to the field of neuropsychiatry.

4 Claims, No Drawings

ω-DIALKYLALKANOIC ACID DERIVATIVES USED TO INDUCE ANTIANOXIC ACTIVITY

This invention relates to ω-dialkylalkanoic acid derivatives having pharmacological and bio-chemical activities and to therapeutic compositions containing them.

The invention also relates to the process for preparing the said compositions and to the preparation of such ω-dialkylalkanoic derivatives when there are novel.

The active compounds of the invention can be represented by the general formula:

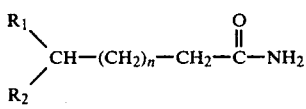   I in which $R_1$ and $R_2$, which can be the same or different, each represent an alkyl radical having from 1 to 4 carbon atoms and n represents 0, 1, 2 or 3.

As will be described in greater detail further on, it has been found that the ω-dialylalkanoic acid derivatives of formula I are endowed, to various degrees, with bio-chemical and pharmacological activities and more particularly with anticonvulsant and antianoxic properties and a competitive inhibitory action with respect to γ-aminobutyric α-ketoglutaric transaminase.

Hence, the compounds of the invention will constitute particularly valuable agents for treating various kinds of central neurological disorders whether resulting or not from cerebral ischemia as well as disorders relating more particularly to the field of neuropsychiatry.

Another object of the invention relates to pharmaceutical and veterinary compositions containing as active ingredient at least one ω-dialkylalkanoic acid derivative of formula I in association with a pharmaceutical carrier or excipient therefor.

Furthermore, another object of the invention is to provide a method of treating central neurological disorders whether resulting or not from cerebral ischemia and including, in particular, convulsive states and seizures and disorders relating to the field of neuropsychiatry in a host in need of such treatment, such method comprising the administration to said host of an effective does of at least one ω-dialkylalkanoic acid derivative of formula I.

Daily dosage will preferably be between 200 and 1500 mg of active principle by any route for a human being weighing 60 kg.

Amongst the compounds of formula I hereabove, a certain number are covered by the general terminology of British Pat. No. 760,114 without being specifically cited therein. A particular example of such a compound is 3-n-propylhexanamide which must nevertheless be regarded as a novel product.

Hence, another object of the present invention relates to novel compounds represented by the general formula:

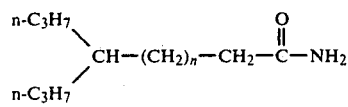   Ia in which n represents 0, 1 or 2.

The derivatives of formula I will be prepared by reacting ammonia with an acyl chloride of formula:

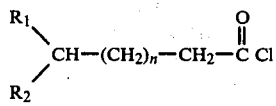   II in which $R_1$, $R_2$ and n have the same meaning as given above for formula I at a temperature between −15° C. and 0° C. and in an appropriate medium, for example, toluene, to obtain the amides of formula I.

In accordance with another procedure, the compounds of formula I in which n represents 0 or 1 can be obtained by hydrolysing, at a temperature between 80° and 85° C., a nitrile of general formula:

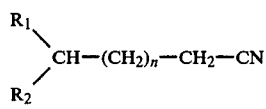   III in which $R_1$ and $R_2$ have the same meaning as given above and n represents 0 or 1, with an 80% by weight solution of sulphuric acid to obtain the required amides of formula I.

The nitriles of formula III can be obtained starting from acids of general formula

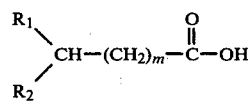   IV in which $R_1$ and $R_2$ have the same meaning as given above and m represents 0 or 1.

These acids of formula IV are first transformed into their acid chloride by reacting with thiony chloride in N,N-dimethylformamide at a temperature between room-temperature and 70° C. and then by esterifying with methanol the chloride so obtained, the esterification taking place at the reflux temperature of the medium.

The methyl ester so obtained is then reduced with a potassium borohydride/lithium chloride mixture in tetrahydrofuran to obtain an alcohol of general formula:

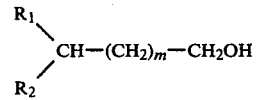   V in which $R_1$, $R_2$ and m have the same meaning as given above.

The alcohol of formula V is then reacted with benzenesulphochloride at room-temperature and in an acid acceptor, for example pyridine, to provide the benzenesulphonate derivatives of general formula:

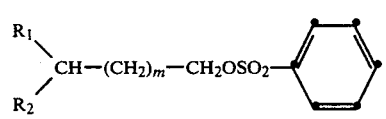   VI in which $R_1$, $R_2$ and m have the same meaning as given above, which are further submitted to the action of sodium or potassium cyanide in an appropriate solvent, for example dimethylsulphoxide, at a temperature between 70° and 90° C. to obtain the nitriles of formula III.

As regards the chlorides of formula II, these will be prepared by reacting thionyl chloride with the corresponding acids. These acids will be obtained in accordance with the procedure described in U.S. Pat. No. 4,025,649 or in accordance with the process described hereunder:

(a) When n represents 0 or 1, by hydrolysing an amide of general formula:

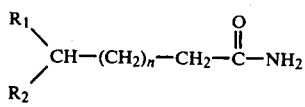

VII in which $R_1$ and $R_2$ have the same meaning as given above and n represents 0 to 1, the hydrolysis being carried out with an 80% by weight solution of sulphuric acid in the presence of sodium nitrite at a temperature of 55° C.±5° to obtain the required acid.

The amides of formula VII are in fact compounds of formula I for which processes of preparation are described above.

(b) When n represents 2 or 3 by reacting a benzenesulphonate derivative of formula VI in which $R_1$ and $R_2$ have the same meaning as given above and m represents 1 or 2 with diethyl malonate in the presence of sodium hydride and in a polar solvent, such as N,N-dimethylformamide, to obtain an ester. This ester is then saponified in the presence of sodium or potassium hydroxide to obtain a salt which is reacted with a strong acid, for example 36%-hydrochloric acid, to obtain the desired malonic acid derivative of general formula:

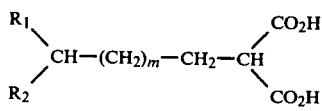

VIII in which $R_1$, $R_2$ have the same meaning as given above and m represents 1 or 2, which is subsequently decarboxylated, at a temperature between 150° C. and 190° C. to provide the required acid.

The benzenesulphonates of formula VI in which m represents 2 can be obtained in accordance with the same procedure as that described with respect to the other derivatives of formula VI in which m represents 0 or 1.

Most of the central nervous system disturbances such as epilepsy are recognized as being chronic diseases requiring, for this reason, regular and prolonged treatment.

Therefore, therapeutic disadvantages which, at first glance, appear to be of minor importance can, in the course of time, become a source of considerable inconvenience necessitating the abandonment of a particular medication and its replacement by an equivalent.

Neurotropic agents of extremely high value have been described in U.S. Pat. No. 4,025,649. Some of them are dialkylpropionic, dialkylbutyric and dialkylvaleric acids and alkali metal salts thereof which are disclosed as possessing anticonvulsant and antianoxic properties and a competitive inhibitory action with respect to γ-aminobutyric α-ketoglutaric transaminase Although these products are of undeniable value, their daily therapeutic dose in the human being is relatively high, in the region of 1000 mg and even more.

At such doses, it is quite evident that undesirable side-effects can occur and this disadvantage must be given serious consideration. For example, the possibility of prolonged administration of such compounds could be endangered to untoward effects on the organism such as, for example, hepatic disorders. Furthermore, the derivatives of this U.S. patent, administered by oral route, whether in the form of an acid or of an alkali metal salt are nevertheless present in the acid form in the gastro-intestinal tract which can lead to irritation in this region. It is well known that such a disadvantage can be avoided by using, for example, enteric-coated units of administration, such as a tablet coated with an enteric film.

In the present case, the addition of supplementary ingredients in the form of an enteric-coating film increases the volume of the tablet to a critical degree. This volume is already considerable at the outset owing to the large amount of active ingredient. When an enteric-coating is added the volume of the tablet is so great that administration to the patient becomes a source of considerable discomfort particularly in the case of young children and elderly people.

These various disadvantages can be avoided or at least greatly reduced by using either a smaller amount of active ingredient per administration unit or a lower daily dosage than that recommended for the compounds of U.S. Pat. No. 4,025,649.

It is thus of prime importance to possess pharmacological agents presenting neurotropic properties at doses inferior to those of the compounds of U.S. Pat. No. 4,025,649 in order to diminish the volume of the administration units, the number of administration units per dose and the potential risk of undesirable side-effects.

It has been quite surprisingly found that by replacing the alkali metal atom, for example the sodium atom, present in the metal salts of U.S. Pat. No. 4,025,649 by an $NH_2$ radical, the anticonvulsant action of the salts of the U.S. Patent is enhanced to a very significant degree, which it was quite impossible to foresee from the state of the art.

Pharmacological studies have furthermore shown that the amides of the invention are also less sedative at antiepileptic doses than di-n-propylacetamide, a well-known antiepileptic and psychotropic agent.

Thus, the compounds of formula I will be less likely to induce undesirable side-effects at anticonvulsant doses than di-n-propylacetamide. Such undesirable side-effects can take the form, for example, of a certain degree of somnolence and loss of the power to concentrate.

Furthermore, it has been unexpectedly found that the amides of the acids of U.S. Pat. No. 4,025,649 present a valuable antianoxic activity, which for some of them is superior to that registered with regard to di-n-propylacetamide and sodium di-n-propylacetate, another well known antiepileptic and antianoxic agent.

In addition, compounds of the invention have been found to be less toxic than the corresponding alkali metal salts of U.S. Pat. No. 4,025,649.

These properties, when taken as a whole, are likely to render the compounds of the invention useful for treating different kinds of central nervous system disturbances and disorders relating to the field of neuropsychiatry while at same time avoiding the disadvantages presented by the derivatives of the U.S. Patent in question.

As an example of such central nervous system disturbances or of disorders induced by central neurological dysfunction, the following can be cited: convulsive states and seizures such as epilepsy, choreic states such as Huntington's chorea, difficulty with respect to memory, balance and fixing the attention, as well as dizziness, decrease of arterial pressure, cephalalgia and comatose states.

Neuropsychiatric disturbances and dysfunction of the central nervous system, whether of ischemic origin or not, constitute one of the most widespread pathological disorders at the present time.

For this reason, it is very difficult for the doctor to choose, amongst the various drugs at his disposal, that which will be effective for the particular case under treatment. When faced with a case of epilepsy, for example, the neurologist is often obliged to feel his way by trying several drugs, one after the other, until he discovers the most suitable medication.

From this point of view, the compounds of the invention will constitute valuable additions to the therapeutic arsenal at the disposal of the doctor and, if necessary, will provide useful replacement medication for a drug which has become ineffective for any reason such as, for example, a change in the state of the patient or habituation.

The compounds of the present invention which have been found to be particularly valuable as neuropsychotropic or neurotropic agents and, in particular, as antiepileptics are:

3-n-Propyl-hexanamide
4-n-Propyl-heptanamide
5-n-Propyl-octanamide

Pharmacological trials have been undertaken with a view to determining the pharmacological properties of the compounds of the invention. The results of some of these tests are indicated below.

I. ANTICONVULSANT ACTIVITY

(1) β-Mercaptopropionic acid seizure

β-Mercaptopropionic acid is an inhibitor of glutamate decarboxylase (G.A.D.), an enzyme which catalyses the transformation of glutamate into γ-aminobutyric acid (GABA). As a consequent of this, a decrease in the GABA lever occurs together with generalized tonico-clonic seizures 3 to 4 minutes after administration.

In the present test, β-mercaptopropionic acid was administered intraperitoneally to batches of 10 male mice, at a dose of 70 mg/kg, 30 minutes after oral administration of a dose of the compound to be studied. The percentage of animals protected against the tonic seizure was registered 15 minutes after administration of the β-mercaptopropionic acid.

The $ED_{50}$ of compounds of the invention is given hereunder in comparison with that registered with respect to the corresponding sodium salts:

$$\begin{array}{c} n\text{-}C_3H_7 \\ \phantom{n\text{-}C_3H_7}\diagdown \\ \phantom{n\text{-}C_3H_7}\phantom{xx}CH-(CH_2)_n-CH_2-\overset{\overset{O}{\|}}{C}-Y \\ \phantom{n\text{-}C_3H_7}\diagup \\ n\text{-}C_3H_7 \end{array}$$

| Value of Y | n | $ED_{50}$ in mg/kg |
|---|---|---|
| ONa | 0 | 168 |
| NH$_2$ | 0 | 106 |
| ONa | 2 | 273 |
| NH$_2$ | 2 | 129 |

These results clearly show that the dose of amide of the invention which protects 50% of the animals against the β-mercaptopropionic acid seizure is inferior to the dose of the corresponding sodium salt required to produce an equivalent effect.

In an other comparative test, the $ED_{50}$ of sodium di-n-propylacetate was found to be 175 mg/kg.

(2) Pentylenetetrazol seizure

This test, performed in mice by oral route, is identical to that described in U.S. Pat. No. 4,025,649.

The $ED_{50}$ registered 15 minutes after administration of the pentylenetetrazol are set out below in comparison with the results obtained with regard to the corresponding sodium salts.

$$\begin{array}{c} n\text{-}C_3H_7 \\ \phantom{n\text{-}C_3H_7}\diagdown \\ \phantom{n\text{-}C_3H_7}\phantom{xx}CH-(CH_2)_n-CH_2-\overset{\overset{O}{\|}}{C}-Y \\ \phantom{n\text{-}C_3H_7}\diagup \\ n\text{-}C_3H_7 \end{array}$$

| Value of Y | n | $ED_{50}$ in mg/kg |
|---|---|---|
| ONa | 0 | 95 |
| NH$_2$ | 0 | 65 |
| ONa | 1 | 119 |
| NH$_2$ | 1 | 104 |
| ONa | 2 | 172 |
| NH$_2$ | 2 | 121 |

In the same conditions, di-n-propylacetamide gave an $ED_{50}$ of 46 mg/kg.

II. ANTIANOXIC ACTION

Anoxia in confined space

Batches of 15 male mice were treated with a dose of a compound to be studied. After that, each animal was placed in a hermetically sealed box of 200 cm$^3$. The animal was considered to be dead when it had stopped breathing.

The increase in the period of survival was then noted in % in comparison with the controls.

The results obtained with compounds of the invention, at an intraperitoneal dose of 75 mg/kg, are given hereunder:

$$\begin{array}{c} n\text{-}C_3H_7 \\ \phantom{n\text{-}C_3H_7}\diagdown \\ \phantom{n\text{-}C_3H_7}\phantom{xx}CH-(CH_2)_n-CH_2-\overset{\overset{O}{\|}}{C}-Y \\ \phantom{n\text{-}C_3H_7}\diagup \\ n\text{-}C_3H_7 \end{array}$$

| Value of Y | n | % of increase in survival time |
|---|---|---|
| NH$_2$ | 1 | 15 |
| NH$_2$ | 2 | 64 |

A comparative test carried out with sodium di-n-propylacetate only gave an increase in survival time of 32% at a dose of 200 mg/kg also administered by intraperitoneal route. In the same conditions 50 mg/kg of di-n-propylacetamide by intraperitoneal route provides an increase in survival time of 12%.

III. TOXICITY

Acute toxicity tests carried out in mice showed that, at the dose of 1000 mg/kg by oral route, the death rate provoked by 3-n-propyl-hexanamide was 0%.

In a comparative test, 80% of deaths were registered with an oral dose of 1000 mg/kg of sodium 3-n-propyl-hexanoate.

Therefore, the toxic dose is far higher than the anticonvulsant dose in the case of compounds of the invention than with sodium 3-n-propyl-hexanoate.

Similarly, the compounds of the invention were found to be less neurotoxic than the corresponding sodium salts namely they are less likely to provoke disturbances of the neuromuscular functions or sedative effects at anticonvulsant doses than the corresponding sodium salts.

In this connection, the test known as the rota rod test (BOISSIER-Therapie 1958, XIII pp. 1074–1118) was carried out with mice.

This test enables the animal's ability to coordinate its movements on a turning rod to be evaluated. Comparative tests were also performed with the corresponding sodium salts. The following results are expressed in % of failures in the test at the given times:

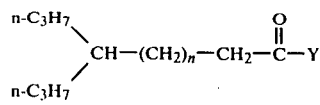

(a) 15 min. after administration of 500 mg/kg by oral route:

| Value of Y | n | % of failures |
| --- | --- | --- |
| ONa | 0 | 30 |
| NH$_2$ | 0 | 30 |
| ONa | 2 | 20 |
| NH$_2$ | 2 | 0 |

A similar test carried out with 170 mg/kg of di-n-propylacetamide by oral route showed 50% of failures, 15 minutes after administration.

When comparing the ED$_{50}$ obtained in the pentylenetetrazol seizure test to the neurotoxic dose found hereabove, it can be observed that the neurotoxic dose in question is always farther removed from the anticonvulsant dose in the case of the compounds of the invention than in the case of the corresponding sodium salts or of di-n-propylacetamide.

(b) 30 min. after administration of 500 mg/kg by oral route:

| Value of Y | n | % of failures |
| --- | --- | --- |
| ONa | 0 | 30 |
| NH$_2$ | 0 | 10 |

(c) 15 min. after administration of 100 mg/kg by intraperitoneal route:

| Value of Y | n | % of failures |
| --- | --- | --- |
| ONa | 1 | 30 |
| NH$_2$ | 1 | 0 |

(d) 30 min. after administration of 100 mg/kg by intraperitoneal route:

| Value of Y | n | % of failures |
| --- | --- | --- |
| ONa | 2 | 100 |
| NH$_2$ | 2 | 50 |

It will be appreciated that for therapeutic use the compounds of the invention will normally be administered in the form of a pharmaceutical or veterinary composition in a dosage unit form appropriate to the required mode of administration, the composition comprising as active ingredient at least one compound of the invention in association with a pharmaceutical carrier or excipient therefor. For oral administration, the composition may take the form of, for example, a coated or uncoated tablet, a hard- or soft-gelatin capsule, a suspension or a syrup. The composition may alternatively take the form of a suppository for rectal administration, or of a solution or suspension for parenteral administration.

When in dosage unit form, the composition may contain from 100 to 300 mg of active ingredient per dosage unit for oral administration, from 200 to 600 mg of active ingredient per dosage unit for rectal administration or from 50 to 200 mg of active ingredient for parenteral administration.

The therapeutic compositions of the invention will be prepared by associating at least one of the compounds of formula I with at least one appropriate carrier or excipient therefor. Examples of suitable carriers or excipients are: talc, magnesium, stearate, lactose, saccharose, colloidal silica, carboxymethylcellulose, starches, kaolin, levilite, mannitol, cocoa butter.

The following Examples illustrate the preparation of the compounds of the invention and of a suitable therapeutic composition.

EXAMPLE 1

Preparation of 3-n-propyl-hexanamide (a) Methyl 2-n-propyl-pentanoate

Into a perfectly dry flask, were introduced, at room-temperature, 142.8 g of thionyl chloride and 2 ml of N,N-dimethylformamide. While stirring, 144.2 g (1 mol) of 2-n-propyl-pentanoic acid were progressively added, the mixture being maintained at room-temperature. This temperature was maintained for 90 to 120 minutes after the operation of introduction was over and the mass was then heated to 70° C. until the gases were eliminated.

The temperature was brought down to room-temperature and 96 g of methanol were progressively added. The medium was heated to reflux and maintained for 60 minutes under total reflux.

After cooling to room-temperature, the mixture was hydrolysed by adding 400 g of distilled water. The aqueous phase was decanted and the organic layer was washed successively with a 5%-aqueous solution of sodium bicarbonate to pH=8–9 and then with water to neutrality. The mixture was again decanted, dried and distilled under vacuum on a water-bath (55°±5° C.) using a rotatory evaporator (p=±20 mm Hg).

Yield: 95%.

In this manner, methyl 2-n-propyl-pentanoate was obtained in crude form.

Using the same method as that described above, methyl 3-n-propyl-hexanoate was prepared with a yield of 96%.

(b) 2-n-Propyl-pentanol

Into a perfectly dry flask, 800 to 850 ml of anhydrous tetrahydrofuran were introduced at room-temperature together with 81 g (1.5 mol) of potassium borohydride and 63.75 g (1.5 mol) of lithium chloride. Stirring was maintained for 30 minutes and then 158.2 g (1 mol) of crude methyl 2-n-propyl-pentanoate were introduced in one operation. The mixture was heated to reflux and so maintained for 4 hours. After cooling to room-temperature, 180 to 200 ml of glacial acetic acid were progressively introduced while maintaining the temperature $\leq 40°$ C. to obtain a pH=5–6. The medium was hydrolysed with 1500 g of distilled water, the organic phase was decanted out and the aqueous phase was extracted with two fractions, each of 500 ml, of ethyl acetate. The organic phases were collected and washed with 2 fractions, each of 500 ml, of distilled water to neutrality. After drying on sodium sulphate, the solvent was eliminated with a rotatory evaporator.

The crude alcohol so obtained was rectified at 100° C. under vacuum (p=50–55 mm Hg).

In this manner 2-n-propyl-pentanol was obtained in a yield of 86%.

Using the same method as that described above, 3-n-propyl-hexanol was prepared with a yield of 81%. This product was rectified at 130° C. under 50 mm Hg.

(c) 1-Benzenesulphonate-2-n-propyl-pentane

Into a perfectly dry flask, were introduced at room-temperature 130.2 g (1 mol) of 2-n-propyl-pentanol and 316.4 g (4 mols) of anhydrous pyridine. While stirring, 194.25 g (1.1 mol) of benzenesulphochloride were progressively added at a temperature $\leq 20°$ C. The medium was maintained for 5 hours at room-temperature and then hydrolysed by adding 800 g of distilled water and 240 ml of 36%-hydrochloric acid. The mixture was then extracted with 3 fractions, each of 200 ml, of ethyl ether, the organic fractions were collected and washed with 300 g of distilled water to neutrality. After drying, on sodium sulphate, the solvent was eliminated under vacuum at 55° C.±5° with a rotatory evaporator.

In this manner, crude 1-benzenesulphonate 2-n-propyl-pentane was obtained in the form of an oil.

Yield: 82.5%.

Using the same procedure as that described above, 1-benzenesulphonate-3-n-propyl-hexane was obtained in a yield of 84%.

(d) 3-n-Propyl-hexanenitrile

Into a flask, 550 to 600 ml of dimethylsulphoxide were introduced at room-temperature together with 270.3 (1 mol) of 1-benzenesulphonate-2-n-propyl-pentane and 73.5 g (1.5 mol) of sodium cyanide. While stirring, the mass was heated to 90° C. and maintained at this temperature for 90 minutes after which it was brought down to room-temperature. The medium was hydrolysed with 1650 to 1800 ml of distilled water and extracted with 3 fractions, each of 700 ml, of ethyl ether. The ethereal extracts were collected, dried on sodium sulphate and the solvent was eliminated with a rotatory evaporator. The nitrile was then rectified under vacuum at a pressure of 12 to 15 mm Hg and at a temperature of 75°–80° C.

In this manner, 3-n-propyl hexanenitrile was obtained in a yield of 92%.

Using the same procedure as that described above, 4-n-propyl-heptanenitrile was obtained in a yield of 95.4%.

This product was rectified at 100°–104° C. under 15 mm Hg.

(e) 3-n-Propyl-hexanamide

Into a flask 71 g of distilled water and 421 g of 95%-sulphuric acid were introduced at room-temperature which provided 500 g of an 80%-solution of sulphuric acid.

While stirring, 139.2 g (1 mol) of 3-n-propyl-hexanenitrile were added. The mixture was heated to 80° C. and maintained at this temperature for 2 hours. After cooling to room-temperature, the medium was hydrolysed while stirring with 1500 g of distilled water for 1 hour. The crude product so obtained was suction-filtered and taken up, while stirring for 1 hour at room-temperature, with 1500 g of distilled water. The medium was again suction-filtered, washed and dried to constant weight in a drying-oven under vacuum.

The purification of the crude amide so obtained was carried out as follows: 157.3 g (1 mol) of crude amine were dissolved in 157 ml of dichlorethane by heating under reflux. The mixture was filtered when hot, rinsed with a minimum amount of warm dichlorethane and allowed to crystallize by cooling under stirring. After being maintained at $-5°/-10°$ C. for 2 hours, the medium was suction-filtered, rinsed with a minimum amount of iced dichlorethane and dried to constant weight at 40° C. in a drying-oven under vacuum.

In this manner, 3-n-propyl-hexanamide was obtained. M.P.: 112° C.

Using the same procedure as that described above, 4-n-propyl-heptanamide was prepared.
M.P: 61° C.

EXAMPLE 2

Preparation of 5-n-propyl-octanamide

(a) Diethyl 3-n-propyl-hexanoylmalonate

Into a perfectly dry flask, were introduced, at room-temperature, 176 g of diethylmalonate and 400 ml of N,N-dimethylformamide. While maintaining the reaction medium at room-temperature, 48 g of 50%-sodium hydride were progressively added. When no more gas was given off, 284.4 g of 1-benzenesulphonate-3-n-propyl-hexane was rapidly added in one operation. The mass was brought to 90° C.±10° for 1 hour, cooled to room-temperature and hydrolysed by adding 1200 g of distilled water. The malonic ester was extracted with 3 fractions, each of 400 ml, of ethyl ether and the ethereal phases were collected and washed with water. After drying on sodium sulphate, the solvent was eliminated under reduced pressure with a rotatory evaporator. The crude ester was distilled under a reduced pressure of 2 mm Hg to an inner temperature of 100° C. and the highest fraction was eliminated.

In this manner, diethyl 3-n-propyl-hexanoylmalonate was obtained.

Yield: 81%.

(b) 5-n-Propyl-octanoic acid

Into a flask, were introduced 280 g of a 50%-aqueous solution of potassium hydroxide, 286 g of diethyl 3-n-propyl-hexanoylmalonate and 100 ml of methanol. While stirring, the mixture was heated to reflux and so maintained for 1 hour. The alcohols were eliminated and the medium was diluted with 400 g of distilled water. The unsaponified products were extracted with 3 fractions, each of 200 ml, of ethyl ether and the malonic acid was formed from its dipotassium salt by adding 250 ml of 36%-hydrochloric acid. The mixture was extracted with 3 fractions, each of 200 ml, of ethyl ether and the ethereal extracts were collected. After drying on sodium sulphate, the solvent was eliminated under reduced pressure. The crude malonic acid derivative was introduced into a 250 ml-flask and, while stirring, the mass was brought to 180°–190° C. under atmospheric pressure.

After complete decarboxylation, the residue was allowed to cool to 100° C. and the 5-n-propyl-octanoic acid so obtained was rectified under reduced pressure. The fraction boiling at 122° C. under 1 mm Hg was collected and the acid so isolated was purified by forming its sodium salt in aqueous solution, extracting the impurities with ethyl ether and liberating the desired acid with 36%-hydrochloric acid. Rectification was again performed and the fraction boiling at 123° C./1 mm Hg was collected.

In this manner, 5-n-propyl-octanoic acid was obtained in a yield of 50% starting from the malonic derivative.

Infra-red spectrum: OH at 3500–2300 cm$^{-1}$ (m,s). C=O at 1710 cm$^{-1}$ (S).

(c) 5-n-Propyl-octanamide

Into a flask, were introduced 300 ml of anhydrous toluene which was cooled to a temperature inferior or equal to $-10°$ C. After that, 40 g (2.35 mols) of gaseous ammonia were added. While maintaining this temperature, there was progressively added a solution of 205 g (1 mol) of crude 5-n-propyl-octanoyl chloride prepared from the corresponding acid and thionyl chloride. Ammonia was again bubbled through the medium which was maintained for 30 minutes at a temperature $\leq -$ ° C. After this operation, 300 g of distilled water were added and the mixture was decanted after the ammonium chloride was dissolved. The organic layer was washed with 2 fractions, each of 300 g, of distilled water to neutrality. The toluene was eliminated under a reduced pressure of about 20 mm Hg and at a temperature of 55° C.±5°. When cooling, the amide crystallized and was then taken up in 100 ml of n-heptane dissolved by heating and allowed to crystallize while stirring. The crystallizing medium was suction-filtered after being kept for 2 hours at $-10°$ C., rinsed with a minimum amount of iced heptane and dried to constant weight in a drying-oven under vacuum and at room-temperature.

In this manner, 130 g of 5-n-propyl-octanamide were obtained in the form of a white powder.

Yield: 70%.

M.P.: 44° C.

Using the same procedure as that described above the following compounds were prepared:

| Compound |
|---|
| 3-n-Propyl-hexanamide |
| M.P.: 112° C. |
| 4-n-Propyl-heptanamide |
| M.P.: 61° C. |

EXAMPLE 3

Tablets containing the following ingredients were prepared in accordance with known pharmaceutical techniques:

| Ingredients | mg per tablet |
|---|---|
| 3-n-Propyl-hexanamide | 100 |
| Mannitol | 69 |
| Corn starch | 60 |
| Colloidal silica | 12 |
| Magnesium stearate | 9 |
| | 250 |

We claim:

1. A method for inducing an antianoxic action in a host in need of such treatment, comprising the administration to said host of an ω-dialkylalkanoic acid derivative of general formula:

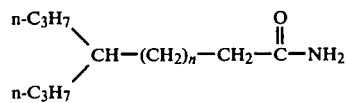

in which n represents 0, 1 or 2, at a daily dosage between 200 and 1500 milligrams of ω-dialkylakanoic acid derivative per 60 kilograms of body weight.

2. Method of claim 1 wherein n is 2.

3. Method of claims 1 or 2 wherein the human dosage of the ω-dialkylalkanoic acid derivative is between 200 and 1500 milligrams per 60 kilograms per day.

4. A pharmaceutical or veterinary composition having an antianoxic action comprising as an essential active ingredient an ω-dialkylalkanoic acid derivative of general formula:

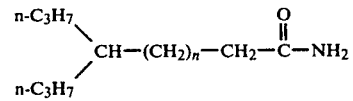

in which n represents 0, 1 or 2, in association with a pharmaceutical carrier, in dosage unit form containing from 50 to 600 milligrams of active ingredients per unit.

* * * * *